United States Patent [19]

Parker

[11] Patent Number: 4,573,968
[45] Date of Patent: Mar. 4, 1986

[54] INFUSION AND BLOOD CHEMISTRY MONITORING SYSTEM

[75] Inventor: Kenneth B. Parker, Alpine, Calif.

[73] Assignee: IVAC Corporation, San Diego, Calif.

[21] Appl. No.: 523,733

[22] Filed: Aug. 16, 1983

[51] Int. Cl.⁴ .............................................. A61B 5/00
[52] U.S. Cl. ..................................... 604/67; 604/49; 604/52
[58] Field of Search ....................................... 604/4–6, 604/65–67, 131, 151–153, 245, 246, 49–53; 128/DIG. 12, DIG. 13, DIG. 3, 637–639, 670, 673–675, 4–6

[56] References Cited

U.S. PATENT DOCUMENTS

| | | | |
|---|---|---|---|
| 2,483,924 | 10/1949 | Mouliner | 604/153 |
| 3,469,577 | 9/1969 | Kater | 128/2.1 |
| 3,498,899 | 3/1970 | Kater et al. | 204/195 |
| 3,910,256 | 10/1975 | Clark et al. | 604/4 |
| 3,993,049 | 11/1976 | Kater | 128/2.06 E |
| 4,094,822 | 6/1978 | Kater | 252/512 |
| 4,240,438 | 12/1980 | Updike et al. | 128/635 |
| 4,340,457 | 6/1982 | Kater | 128/635 |
| 4,411,792 | 10/1983 | Babb | 604/5 |

Primary Examiner—C. Fred Rosenbaum
Assistant Examiner—Karen Kaechele
Attorney, Agent, or Firm—Fulwider, Patton, Rieber, Lee & Utecht

[57] ABSTRACT

A patient infusion and blood chemistry monitoring system is provided for controlled fluid infusion with intermittent interruption for automated drawing of a patient blood sample into contact with one or more electrochemical sensors to obtain blood chemistry determinations, such as measurements of blood electrolytes and the like. The system comprises an infusion pump operated by a control unit to supply a selected fluid to the patient through an infusion line and catheter. The control unit intermittently halts and reverses operation of the infusion pump to draw a patient blood sample through the catheter into contact with the electrochemical sensors positioned along the infusion line within a compact cassette near the patient and then to reinfuse the blood sample into the patient upon resumption of normal infusion operation. The sensors provide electrical input signals representative of patient blood chemistry to an analyzer which alters the signals to an appropriate readable output.

16 Claims, 3 Drawing Figures

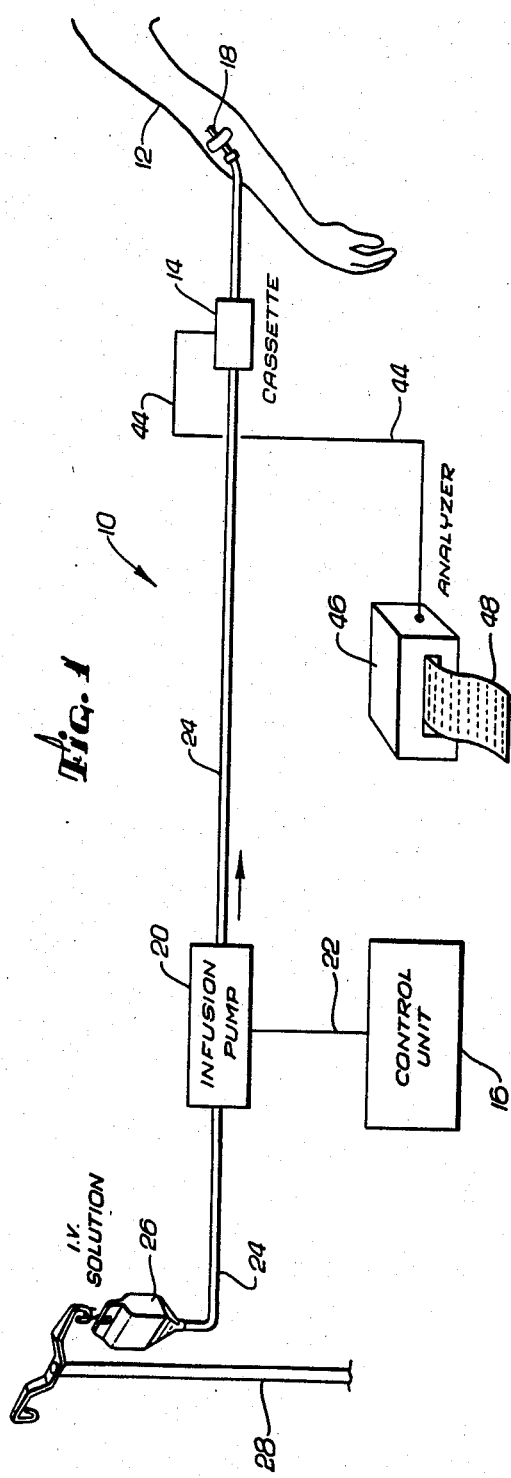
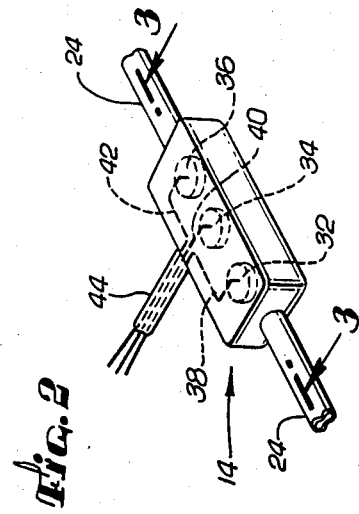
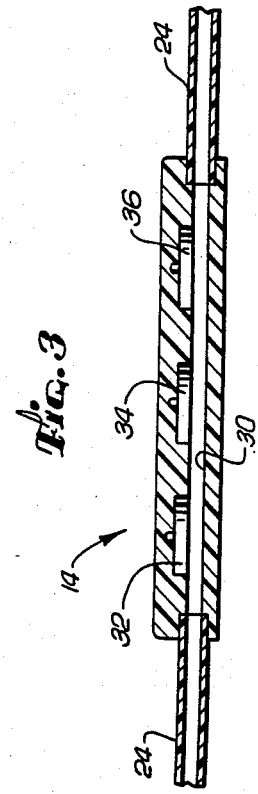

INFUSION AND BLOOD CHEMISTRY MONITORING SYSTEM

BACKGROUND OF THE INVENTION

This invention relates generally to systems and methods for controlling and monitoring the condition of a patient. More specifically, this invention relates to an infusion fluid delivery system including the capability for obtaining periodic bedside measurements of patient blood chemistry.

Fluid infusion delivery systems in general are well known for infusing a selected fluid into a patient at a controlled flow rate and/or pressure. Such infusion delivery systems are used primarily with hospitalized patients to administer a variety of fluids including, for example, saline solutions, nutrients, drugs, and the like. Fluid infusion is normally accomplished by gravity flow and/or in conjunction with automated controllers or pumps through a flexible infusion line and further through a catheter inserted intravenously into the patient.

In recent years, patient blood chemistry and monitoring thereof has been recognized as an important information tool for improved patient care. For example, measurement of blood electrolytes, such as potassium, sodium, calcium, and chloride, can provide the physician with important information regarding patient condition and requisite treatment regimens. In the past, such measurements have been obtained by drawing a patient blood sample and then transporting the sample to an appropriate laboratory facility for analysis. However, blood chemistry levels can change rapidly and dramatically within a short period of time whereby the laboratory test data can be outdated before it can be returned to the attending physician. Moreover, repeated drawing and analysis of patient blood samples with a requisite frequency of perhaps several times each day substantially increases the cost of patient care and further results in significant inconvenience or discomfort to the patient.

Some attempts have been made to design a blood chemistry sensor for intravenous installation to provide continuous or rapid frequency in vivo blood chemistry measurements. See, for example, U.S. Pat. No. 4,340,457 which discloses miniature ion selective electrodes mounted on a catheter or needle structure for direct placement into a patient's bloodstream. However, significant manufacturing problems particularly with respect to sensor miniaturization have been encountered in electrochemical sensors for in vivo use. Moreover, proposed in vivo sensors are subject to contamination from prolonged exposure to patient blood thereby limiting sensor life and accuracy when inserted into the patient's bloodstream.

There exists, therefore, a significant need for a practical and economic blood chemistry monitoring system for obtaining frequent blood chemistry measurements at patient bedside without requiring substantial miniaturization of electrochemical sensors and further without requiring frequent insertion of needles or catheters into the patient. The present invention fulfills these needs and provides further related advantages by providing a combined blood chemistry monitoring and infusion fluid delivery system.

SUMMARY OF THE INVENTION

In accordance with the invention, a patient infusion fluid delivery system is provided for controlled infusion of a selected fluid into a patient and for bedside monitoring of patient blood chemistry at selected intervals. The infusion fluid is supplied to the patient through an infusion line and catheter under the control of a control unit which intermittently halts fluid infusion for a brief time interval during which a patient blood sample is drawn through the catheter into contact with one or more electrochemical sensors. The sensors provide electrical input signals to an analyzer which transforms those signals to a readable output indicative of patient blood chemistry. The control unit then reinfuses the blood sample into the patient and resumes normal infusion operation until the next blood chemistry reading is desired.

In the preferred form of the invention, the control unit comprises a selectively programmable unit for controlling operation of a reversible infusion pump normally to supply the infusion fluid through the infusion line and catheter to the patient at a controlled flow rate. When a blood chemistry measurement is desired, the control unit commands the infusion pump to halt infusion operation. After an appropriate delay period of a few seconds to permit infused fluid to be carried by the patient's bloodstream away from the infusion site, the control unit commands the infusion pump to begin reversed pumping operation to draw the patient blood sample through the catheter and into a relatively compact sensor cassette positioned along the infusion line near the patient, preferably within a few inches of the infusion site.

The sensor cassette supports one or more electrochemical sensors for direct contact with the drawn blood sample, whereupon these sensors provide electrical input signals to a signal analyzer which converts these signals to a usable output. The control unit maintains the blood sample in direct contact with the sensors until the electrical input signals reach a steady state condition, at which time the control unit commands the infusion pump to resume normal infusion operation thereby flushing the blood sample from the cassette and reinfusing the blood sample into the patient with the infusion fluid, followed immediately by resumed supply of the infusion fluid to the patient.

The electrochemical sensors are provided in a suitable form for obtaining the desired blood chemistry measurements. In one preferred form of the invention, the sensors comprise ion selective electrodes generally of the type described in U.S. Pat. Nos. 3,498,899 and 4,340,457 for providing electrical potentials having a magnitude representing concentration of particular blood electrolytes, such as potassium.

Other features and advantages of the present invention will become more apparent from the following detailed description, taken in conjunction with the accompanying drawings, which illustrate, by way of example, the principles of the invention.

BRIEF DESCRIPTION OF THE DRAWINGS

The accompanying drawings illustrate the invention. In such drawings:

FIG. 1 is a diagrammatic illustration depicting an infusion and blood chemistry monitoring system embodying the novel features of the present invention;

FIG. 2 is an enlarged fragmented perspective view illustrating an exemplary sensor cassette for use in the system of FIG. 1; and FIG. 3 is an enlarged fragmented longitudinal section taken generally on the line 3—3 of FIG. 2.

DETAILED DESCRIPTION OF THE PREFERRED EMBODIMENT

As shown in the exemplary drawings, an infusion and blood chemistry monitoring system referred to generally by the reference numeral 10 is provided for controlled supply of a selected infusion fluid into a patient 12, with intermittent interruption during which a patient blood sample is drawn into contact with one or more electrochemical sensors (not shown in FIG. 1) within a compact sensor cassette 14 for obtaining patient blood chemistry measurements. The system 10 may be controlled and operated by a control unit 16 for automatic, programmable regulated supply of infusion fluid and for obtaining blood chemistry measurements at predetermined times.

The infusion and monitoring system 10 of the present invention advantageously integrates components for obtaining blood chemistry measurements with conventional components of an infusion fluid administration system. The combined system 10 utilizes a single catheter 18 which is inserted into the patient 12, typically intravenously, to provide a flow path for fluid infusion and drawing of a patient blood samples, thereby avoiding repeated insertion of needle or catheter structures into the patient as is commonly required with previous blood chemistry monitoring techniques. The system operates automatically without intervention of hospital personnel to draw blood samples at virtually any programmable frequency and to analyze those blood samples at patient bedside to obtain immediately the desired blood chemistry readings. Importantly, electrochemical sensors are provided in an economic form packaged into the sensor cassette 14 which may be disposed after use with a single patient, wherein the sensors are contacted by each patient blood sample only for a few seconds to minimize sensor contamination and thereby enhance sensor accuracy and life.

The combined infusion and monitoring system 10 is shown diagrammatically in FIG. 1 to include the control unit 16 for controlling operation of an infusion pump 20 to correspondingly control fluid infusion and drawing of blood samples. This control unit 16, in the preferred form of the invention, comprises a selectively programmable computer unit for automatically providing a series of command signals via a data cable 22 to the infusion pump 20 which includes appropriate means, such as a computer interface module (not shown), for receiving and interpreting the command signals. The particular specifications for the control unit 16 and computer interface modules or the like, however, may vary widely and will be readily apparent to those skilled in the art whereby these system components are not described in further detail herein.

The infusion pump 20 comprises a volumetric infusion pump of known design for use in intravenous fluid administration systems and including at least some capability for reversible draw and pump operation, with one preferred pump being a Model 1500 volumetric infusion pump sold under the trademark INFU CHECK by IVAC Corporation, San Diego, Calif. This infusion pump 20 is positioned along the length of an infusion line 24 formed commonly of flexible plastic tubing or the like. The upstream end of the infusion line is flow-coupled with a supply of a selected infusion fluid within a container 26 supported upon a stand 28 in an elevated position, wherein this fluid may comprise nutrient solution, drugs, sterile water, or the like. The downstream end of the infusion line is coupled to the catheter 18 which is in turn inserted into the patient. In most instances, the catheter will be inserted into a vein for intravenous fluid infusion, although arterial insertion may be desired in some cases.

During normal fluid infusion operation of the system 10, the control unit 16 appropriately commands the infusion pump 20 to supply the infusion fluid to the patient at a controlled flow rate. At a predetermined time, in accordance with programming of the control unit 16, the control unit 16 signals the infusion pump 20 to halt supply of the infusion fluid. When this occurs, the infusion pump 20 ceases operation and occludes the infusion line 24 against fluid flow in either direction for a relatively short delay period, tyically about five seconds, sufficient to permit the patient's bloodstream to carry infusion fluid away from the infusion site.

After the short delay period, the control unit 16 signals the pump 20 to draw a blood sample whereupon the pump 20 initiates reversed pumping operation to pump infusion fluid in a direction away from the patient. This fluid movement draws a patient blood sample through the catheter 18 and a distal portion of the infusion line 24 into the sensor cassette 14. Conveniently, the cassette 14 can be positioned within a few inches of the patient to keep the drawn blood sample volume to a minimum, such as on the order of two to five milliliters.

The blood sample drawn into the sensor cassette 14 comes into direct contact with the electrochemical sensors which are mounted along an internal cassette flow path 30, with three of said sensors being shown in FIGS. 2 and 3 and designated by the reference numerals 32, 34, and 36. In the preferred form, these sensors comprises relatively small electrodes, such as ion selective electrodes of the general type shown and described in U.S. Pat. Nos. 3,498,899 and 4,340,457, for providing an electrical potential representative of the concentration of selected blood electrolytes, such as potassium, sodium, calcium, chloride, and the like. Alternatively, the sensors may take other forms appropriate for obtaining other selected blood chemistry measurements. Conductors 38, 40, and 42 are connected to the sensors and are collected within a composite signal line 44 for connection of sensor-generated electrical signals to a signal analyzer 46.

In operation of the system 10, the control unit 16 halts drawing operation of the pump 20 to maintain the blood sample within the sensor cassette 14 in direct contact with the sensors 32, 34, and 36 for a period of time, typically about ten to twenty seconds, to permit the electrical signals generated by the sensors to reach a steady state condition. These signals comprise inputs to the analyzer 46 which amplifies and otherwise appropriately alters these signals to a usable and readable output, such as in the form of printed blood chemistry measurements on a strip chart 48, as viewed in FIG. 1. In the case of electrode-type sensors for producing electrical potentials representing concentration levels of selected blood electrolytes, the analyzer 46 may comprise a precision voltmeter for providing precision voltage readings. Alternatively, the analyzer may take other appropriate forms in accordance with the nature of the input signals thereto and may provide other types of outputs, such as, for example, digital displays (not shown) representative of blood chemistry measurements.

After blood sample analysis, the infusion pump 20 is reversed again under command of the control unit 16 to pump infusion fluid once again in a direction toward the patient. This resumes infusion fluid flow through the cassette 14 to flush the cassette flow path 30, which preferably is smoothly contoured to avoid blood sample entrapment. The infusion fluid further acts as the driving medium to reinfuse the blood sample through the catheter 18 into the patient 12, after which the infusion fluid is supplied to the patient for a period of normal infusion operation until a subsequent blood chemistry reading is performed.

The infusion and monitoring system 10 of the present invention thus provides the combined capability of fluid infusion and periodic blood chemistry monitoring directly at patient bedside to provide immediate blood chemistry measurements at programmable time intervals. Both infusion and monitoring are advantageously controlled automatically without requiring intervention by hospital personnel and further without requiring frequent insertion of needle or catheter strucures into the patient.

A variety of modifications and improvements to the infusion and monitoring system of the present invention are believed to be apparent to one skilled in the art. Accordingly, no limitation on the invention is intended, except by way of the appended claims.

What is claimed is:

1. A system for infusing fluid into a patient and for monitoring patient blood chemistry, comprising:
   an infusion line;
   a catheter at one end of said infusion line and adapted for insertion into the patient;
   a reversible infusion pump operable for pumping an infusion fluid through said infusion line and said catheter in a first direction for infusion into the patient;
   a blood chemistry sensor mounted in flow communication with said infusion line near said catheter for providing an indication of patient blood chemistry upon contact with a patient blood sample; and
   control means for controllably interrupting operation of said infusion pump in said first direction to interrupt supply of infusion fluid into the patient for a selected time interval;
   said control means further including means for operating said infusing pump for pumping infusion fluid through said infusion line in a second direction for drawing a patient blood sample through said catheter into contact with said sensor and then to resume operation in said first direction for reinforcing the drawn blood sample through said catheter into the patient followed by resumed infusion of said infusion fluid.

2. The system of claim 1 wherein said control means is programmable for interrupting supply of infusion fluid for said selected time interval at a predetermined frequency.

3. The system of claim 1 wherein said blood chemistry sensor comprises an electrode for providing an electrical signal representative of a selected patient blood chemistry measurement, and further including an analyzer coupled electrically to said sensor and responsive to said electrical signal to provide a readable output representing the selected blood chemistry measurement.

4. The system of claim 1 wherein said blood chemistry sensor is mounted on a sensor cassette having a fluid flow path formed therethrough with said sensor in contact with fluid within said flow path, and including means for coupling said cassette flow path into fluid communication with said infusion line.

5. The system of claim 1 wherein said sensor comprises an ion selective electrode.

6. A system for infusing fluid into a patient and for monitoring patient blood chemistry, comprising:
   an infusion line;
   a catheter at one end of said infusion line and adapted for insertion into the patient, the other end of said infusion line being adapted for connection to a supply of a selected infusion fluid;
   a reversible infusion pump operable in a first direction for controllably pumping the infusion fluid through said infusion line and said catheter into the patient;
   a sensor cassette having a fluid flow path formed therethrough and at least one blood chemistry sensor mounted on said cassette for sensing contact with fluid within said flow path;
   means for coupling the cassette flow path into flow communication with said infusion line at a point along said infusion line near said catheter;
   said reversible infusion pump being operable in a second direction for controllably pumping the infusion fluid in a second direction away from said catheter to draw a patient blood sample through said catheter into the cassette flow path in sensing contact with said at least one sensor, said infusion pump being subsequently operable in the first direction for controllably pumping the infusion fluid toward said catheter to flush the blood sample from the cassette flow path and to reinfuse the blood sample into the patient and to resume supply of the infusion fluid to the patient;
   an analyzer coupled to said at least one sensor and responsive thereto to provide a readable output representing patient blood chemistry measurements; and
   a control unit for operating said infusion pump normally in the first direction to pump the infusion fluid to the patient, said control unit including means for operating said infusion pump in the second direction at predetermined time intervals to draw a patient blood sample.

7. The system of claim 6 wherein said control unit is programmable.

8. The system of claim 6 wherein said control unit further includes means for halting operation of said pump after operation thereof in the first direction to permit the patient's bloodstream to carry infusion fluid within the bloodstream away from said catheter.

9. The system of claim 6 wherein said control unit further includes means for halting operation of said pump after operation thereof in the second direction to hold the drawn blood sample for a predetermined holding time within the cassette flow path.

10. The system of claim 6 wherein said sensor cassette is disposable.

11. A method of infusion fluid into a patient and monitoring patient blood chemistry, comprising the steps of:
    inserting a catheter into the patient;
    infusing a selected infusion fluid through the catheter into the patient by operating a reversible infusion pump in a first direction;

intermittently interrupting supply of the infusion fluid to the patient by interrupting operation of the infusion pump in the first direction; and drawing a patient blood sample through the catheter into sensing contact with a blood chemistry sensor by operating the infusion pump in a second direction and then reinfusing the drawn sample through the catheter into the patient and resuming infusion of the infusion fluid into the patient by resuming infusion pump operation in the first direction.

12. The method of claim 11 including the step of positioning the sensor near the catheter.

13. The method of claim 11 including the steps of flushing the drawn sample from the sensor with infusion fluid during said reinfusing step.

14. The method of claim 11 including the step of programmably controlling the frequency and duration of said infusion fluid interrupting step.

15. The method of claim 11 including the step of initially delaying drawing of the blood sample upon interruption of said infusing step for a period of time sufficient to permit the patient's bloodstream to carry infusion fluid away from the infusion site.

16. The method of claim 11 including the step of holding the blood sample in sensing contact with the sensor for a predetermined time period prior to reinfusion into the patient.

* * * * *